(12) United States Patent
Spencer et al.

(10) Patent No.: US 7,896,840 B2
(45) Date of Patent: Mar. 1, 2011

(54) CATHETER HAVING INTERNAL MECHANISMS TO ENCOURAGE BALLOON RE-FOLDING

(75) Inventors: Steve M. Spencer, Minneapolis, MN (US); Robert Warner, Woodbury, MN (US); Victor L. Schoenle, Greenfield, MN (US); John Blix, Maple Grove, MN (US); Tracee Eidenschink, Wayzata, MN (US); Matt Heidner, Maple Grove, MN (US)

(73) Assignee: Boston Scientific Scimed, Inc., Maple Grove, CA (US)

( * ) Notice: Subject to any disclaimer, the term of this patent is extended or adjusted under 35 U.S.C. 154(b) by 781 days.

(21) Appl. No.: 11/697,133

(22) Filed: Apr. 5, 2007

(65) Prior Publication Data

US 2008/0249464 A1 Oct. 9, 2008

(51) Int. Cl.
*A61M 5/20* (2006.01)
*A61M 29/00* (2006.01)
*A61M 31/00* (2006.01)

(52) U.S. Cl. ............ 604/130; 604/103.01; 604/103.06; 604/101.01

(58) Field of Classification Search ................ 604/130, 604/101.01, 98.01, 101.02
See application file for complete search history.

(56) References Cited

U.S. PATENT DOCUMENTS

| | | | |
|---|---|---|---|
| 5,041,126 A * | 8/1991 | Gianturco | 623/1.15 |
| 5,470,314 A | 11/1995 | Walinsky | |
| 5,645,529 A | 7/1997 | Fagan et al. | 604/101 |
| 5,749,852 A * | 5/1998 | Schwab et al. | 604/103.01 |
| 5,984,946 A | 11/1999 | Gupta | |
| 6,544,224 B1 * | 4/2003 | Steese-Bradley | 604/103.06 |
| 6,988,881 B2 * | 1/2006 | Motsenbocker et al. | 425/392 |
| 7,160,317 B2 * | 1/2007 | Mc Hale et al. | 623/1.11 |
| 2001/0007082 A1 | 7/2001 | Dusbabek et al. | |
| 2002/0032406 A1 * | 3/2002 | Kusleika | 604/101.02 |
| 2002/0183779 A1 | 12/2002 | Vigil | 606/192 |
| 2005/0177130 A1 * | 8/2005 | Konstantino et al. | 604/509 |
| 2008/0015540 A1 * | 1/2008 | Muni et al. | 604/500 |

FOREIGN PATENT DOCUMENTS

| | | |
|---|---|---|
| WO | 9915225 | 4/1999 |
| WO | 0057811 | 10/2000 |
| WO | 2006042260 A2 | 4/2006 |

* cited by examiner

*Primary Examiner*—Nicholas D Lucchesi
*Assistant Examiner*—Ian K Holloway
(74) *Attorney, Agent, or Firm*—Vidas, Arrett & Steinkraus P.A.

(57) ABSTRACT

A balloon catheter that comprises an inner shaft, a balloon and a sleeve that defines a lumen. A portion of the inner shaft is positioned within the lumen and the balloon is engaged to the sleeve at least two engagement points.

22 Claims, 15 Drawing Sheets

CATHETER HAVING INTERNAL MECHANISMS TO ENCOURAGE BALLOON RE-FOLDING

CROSS-REFERENCE TO RELATED APPLICATIONS

Not Applicable

STATEMENT REGARDING FEDERALLY SPONSORED RESEARCH

Not Applicable

FIELD OF THE INVENTION

In some embodiments this invention relates to delivery systems, such as catheter systems of all types, which are utilized in the delivery of such implantable medical devices.

BACKGROUND OF THE INVENTION

Percutaneous transluminal angioplasty (PTA), including percutaneous transluminal coronary angioplasty (PTCA), is a procedure which is well established for the treatment of blockages, lesions, stenosis, thrombus, etc. present in body lumens, such as the coronary arteries and/or other vessels.

Percutaneous angioplasty makes use of a dilatation balloon catheter, which is introduced into and advanced through a lumen or body vessel until the distal end thereof is at a desired location in the vasculature. Once in position across an afflicted site, the expandable portion of the catheter, or balloon, is inflated to a predetermined size with a fluid at relatively high pressures. By doing so the vessel is dilated, thereby radially compressing the atherosclerotic plaque of any lesion present against the inside of the artery wall, and/or otherwise treating the afflicted area of the vessel. The balloon is then deflated to a small profile so that the dilatation catheter may be withdrawn from the patient's vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strength the area, a physician can implant an intravascular prosthesis for maintaining vascular patency, such as a stent, inside the artery at the lesion.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In order to ensure proper catheter withdrawal following angioplasty and/or the delivery of a medical device, embodiments of the present invention are directed to mechanisms which facilitate balloon rewrap about the catheter shaft during deflation of the balloon.

Such mechanisms include sleeves, biasing members, skeletons or frameworks, plungers, tethers, and other mechanisms alone or in combination with one another. In some embodiments a mechanism is engaged to the catheter shaft, the balloon and/or one or more regions of both in order to refold the balloon before withdrawal.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
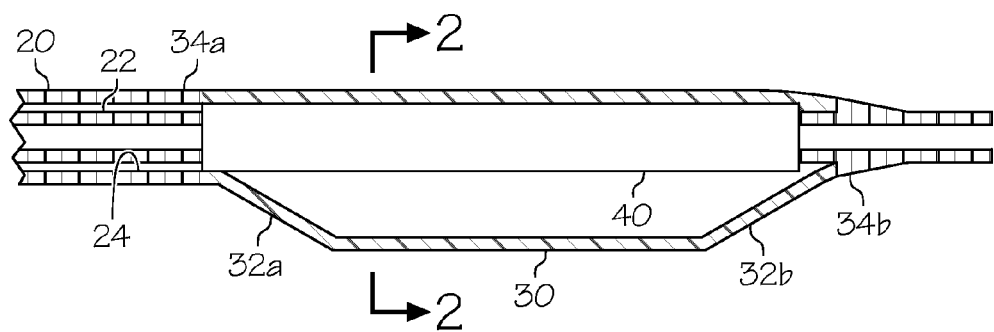
FIG. 1 is a longitudinal cross-section of a balloon catheter with a sleeve positioned around the inner shaft.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

At least one embodiment of the invention is directed to a balloon catheter 10, such as is shown for example in FIG. 1. FIG. 1 shows a longitudinal cross-section of a balloon catheter 10 with a sleeve 40 engaged to the balloon 30. The balloon catheter 10 has an outer shaft 20, an inner shaft 22, a sleeve 40 and a balloon 30. The outer shaft 20 defines an inflation lumen 24. The balloon 30 has a proximal waist 34a, proximal cone 32a, a middle section, a distal cone 32b and a distal waist 34b. The middle section is between the proximal cone 32a and the distal cone 32b of the balloon 30. A sleeve 40 is positioned about the inner shaft 22 between the inner shaft 22 and the balloon 30.

Figure 2:
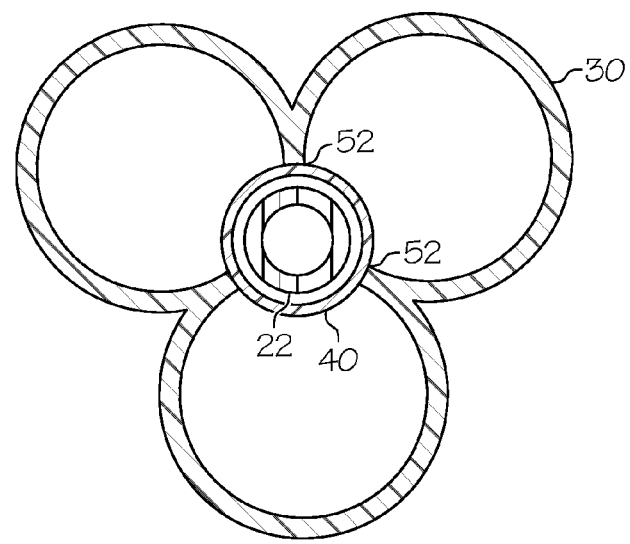
FIG. 2 is a cross-section of the balloon catheter in FIG. 1 taken at line 2-2.

FIG. 2 is a cross-section of the balloon catheter 30 in FIG. 1 taken at line 2-2 showing the balloon 30 crimped onto the sleeve 40 where the sleeve 40 is in an unexpanded state. Note that the sleeve 40 is not fixedly engaged to the inner shaft 22 but it is fixedly engaged to the balloon 30. The sleeve 40 is fixedly engaged to the balloon 30 at three engagement regions 52, each of which extends along the longitudinal length of the sleeve 40, as illustrated in FIG. 1, thereby forming a multi-lobed balloon 30. The number of engagement regions 52 between the balloon 30 and the sleeve 40 depends upon the size of the balloon 30. Thus, it is within the scope of the invention for there to be one, two, three, four, five, six, seven, eight or more engagement regions 52 between the balloon 30 and the sleeve 40. In at least one embodiment, the engagement regions 52 are formed by crimping the balloon 30 onto the sleeve 40.

In this embodiment, there are three engagement regions 52 positioned in a symmetrical manner about the sleeve 40, thereby giving the balloon 30 a propeller like configuration. The engagement regions 52 are symmetrical because the amount of balloon material and therefore the size of the lobes between the engagement regions 52 is the same. In at least one embodiment, symmetrically placed engagement regions 52 cause the symmetrical re-folding of the balloon 30. In at least one embodiment, the symmetrically placed engagement regions 52 lower both the withdrawal and re-cross forces. In at least one embodiment, the engagement regions 52 are not positioned in a symmetrical manner about the sleeve 40.

In at least one embodiment, the engagement regions 52 between the balloon 30 and the sleeve 40 are formed by the heat bonding of compatible materials. In at least one embodiment, formation of the engagement regions 52 between the balloon 30 and the sleeve 40 is enhanced by a coating of adhesive material. In at least one embodiment, at least a portion of the inner surface of the balloon 30 has a layer of adhesive. Examples of adhesives include, but are not necessarily limited to, the use of thermoplastic, water-based, reactive chemistries and solvent based adhesives. In at least one embodiment, at least a portion of the sleeve 40 has a layer of either thermoplastic adhesives, thermoplastic pressure sensitive adhesives, water based pressure sensitive adhesives, or thermoset adhesives. In at least one embodiment, the sleeve 40 is co-extruded with either thermoplastic adhesives, thermoplastic pressure sensitive adhesives, water based pressure sensitive adhesives, or thermoset adhesives.

Thermoplastic adhesives may be based on polymers including, but not limited to, polyolefin's, including polyethylene and polypropylene, polyamides, polyurethanes, polyesters, polyacrylates, elastomeric block co-polymers, and any co-polymers axed terpolymers thereof. Ethylene vinyl acetate, ethylene methyl acrylate, ethylene-n-butyl acrylate, and so forth, are commonly employed copolymers of ethylene, and homopolymers of ethylene and propylene are commonly employed in thermoplastic adhesives as well. Another class or ethylene copolymers include those referred to in the art as interpolymers of ethylene having at least one C3 to C2O alphaolefin. Thermoplastic adhesive compositions may suitably also include tackifying resins, plasticizers, oils, waxes, antioxidants, and any combination thereof, as well as other additives known to those of skill in the art.

Thermoplastic pressure sensitive adhesives commonly incorporate rubbery block copolymers such as the styrenic block copolymers including, but not limited to, styrene-isoprene-styrene (SIS), styrene-butadiene-styrene (SBS), styrene-ethylene/propylene-styrene (SEPS), styrene-ethylene/butylene-styrene (SEBS), styrene-isobutylene-styrene (SIBS), and so forth.

Water based pressure sensitive adhesives commonly incorporate polyacrylic polymers such as styrene-acrylic copolymer, vinyl-acrylic, vinyl ester/vinyl acetate/acrylic; ethylene vinyl acetates, polyurethanes; polyurethane-acrylic hybrids; polyanudes; styrene-butadiene rubbers; polychloroprenes; crylonitrile-butadiene-styrene; polyisoprenes; polyisobutylene; polyurea; natural latex; polysaccharides; gum resins; polyvinyl alcohols; and combinations thereof.

Thermoset adhesives which are cured by heat, chemical reaction or and/or irradiation, may also be employed herein. There are a variety of thermoset adhesives including heat curing, moisture curing and UV curing, for example. Many such adhesives also come in one and two-part formulations. Suitable UV curable compounds include those having (meth) acrylate functionality such as epoxy (meth)acrylates, urethane (meth)acrylates, polyester (meth)acrylates, acrylic (meth)acrylates, and so forth. Examples of suitable moisture cures include polyurethanes and polyorganosiloxanes. In addition examples of suitable two-component curing systems may include epoxies, polyurethanes, acrylics, and so forth.

Figure 3:
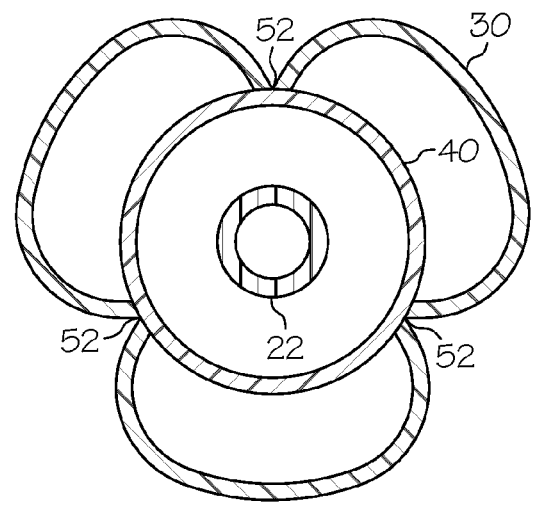
FIG. 3 is a cross-section of the balloon catheter in FIG. 1 taken at line 2-2 where the sleeve is partially inflated.
Figure 4:
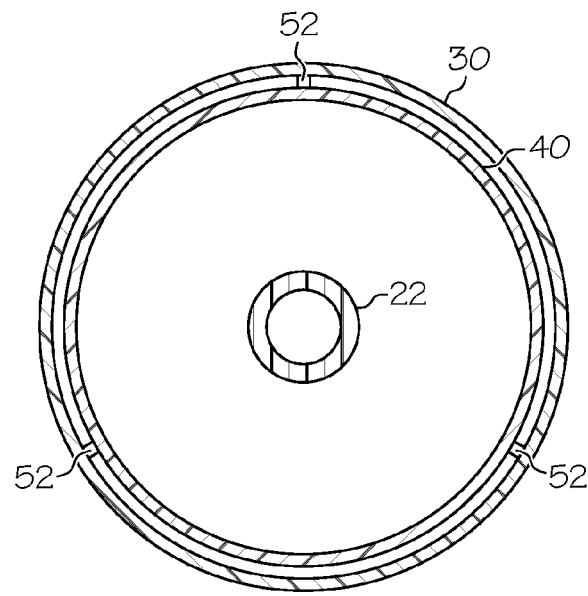
FIG. 4 is a cross-section of the balloon catheter in FIG. 1 taken at line 2-2 where the sleeve is fully inflated.

The sleeve 40 has different expansion states, an unexpanded state, an intermediate expanded state and an expanded state, which are illustrated in FIGS. 2, 3, and 4 respectively. The sleeve 40 is in an intermediate expanded state when it is in neither an unexpanded state nor an expanded state. The expansion state of the sleeve 40 depends upon the inflation of the balloon 30 by the inflation media. Thus, when the inflation media is withdrawn from the balloon 30, the sleeve 40 transitions from an expanded state to an unexpanded state.

Figure 5:
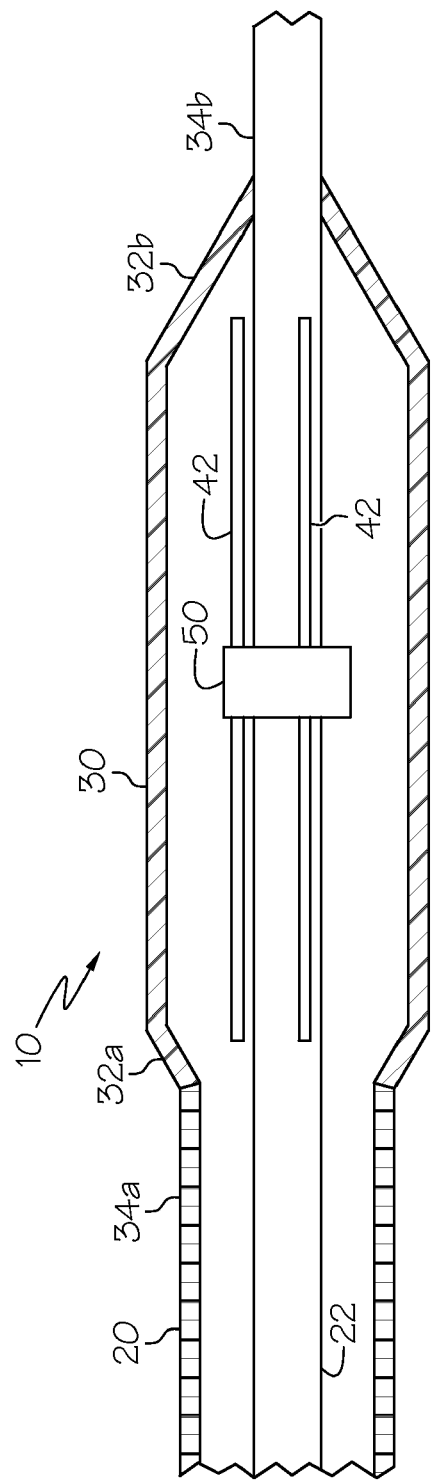
FIG. 5 is a longitudinal cross-section of a balloon catheter with both the biasing members and the balloon in an unexpanded state.

FIG. 5 is a longitudinal cross-section of a balloon catheter 10 embodiment with at least one biasing member 42. It is within the scope of the invention for the balloon catheter 10 to have one, two, three, four, five, six, seven, eight or more biasing members 42. The balloon catheter 10 has an outer shaft 20, an inner shaft 22, a band 50, three biasing members 42 and a balloon 30. The outer shaft 20 defines an inflation lumen 24. The balloon 30 has a proximal waist 34a, proximal cone 32a, a middle section, a distal cone 32b and a distal waist 34b. The middle section is between the proximal cone 32a and the distal cone 32b of the balloon 30. The balloon 30 is positioned about the balloon region of the inner shaft 22 and has an expanded state, an intermediate expanded state and an unexpanded state. The balloon region of the inner shaft 22 extends from the proximal end of the proximal waist 34a of the balloon 30 to the distal end of the distal waist 34b of the balloon 30. In FIG. 5, the balloon 30 is in an unexpanded state and the biasing members 42 are in a first unexpanded state. In this embodiment, when the biasing members 42 are in the first unexpanded state the biasing members 42 extend alongside the inner shaft 22.

In this embodiment, a band 50 is positioned about the balloon region of the inner shaft 22 and engages a portion of the biasing members 42 to the inner shaft 22, thereby holding the biasing members 42 in position about the circumference of the inner shaft 22. In at least one embodiment, the band 50 is positioned about the middle of the balloon region of the inner shaft 22, as illustrated in FIG. 5. Also, the band 50 engages the middle portion of each biasing members 42 to the inner shaft 22. However, the band 50 may engage any portion of an individual biasing member 42 so long as at least one end of the biasing member 42 engages at least one balloon cone 32. Note that the band 50 can have any longitudinal length and shape so long as it engages the biasing member(s) 42 and allows the biasing member(s) 42 to engage the cones of the balloon 30 as described below. In at least one embodiment, the band 50 is a wire.

In at least one embodiment, the biasing members 42 each have a first end engaged to the band 50. In this embodiment, there are two sets of biasing members 42, a proximal set engaged to the proximal side/end of the band 50 and a distal set engaged to the distal side/end of the band 50. The second ends of the proximal set of biasing members 42 in the expanded state are engaged to the proximal cone 32a while the second ends of the distal set of biasing members 42 in the expanded state are engaged to the distal cone 32b. Note that the biasing members 42 can have any shape so long as the biasing members 42 help with balloon re-wrap as discussed below. Also note that the length of the biasing members 42 depends upon the length between the proximal cone 32a and the distal cone 32b.

In at least one embodiment, the biasing members 42 are engaged to the inner shaft 22. Thus, in this embodiment there is no band 50. In this embodiment, there are two sets of biasing members 42, a proximal set and a distal set. The first ends of the all the biasing members 42 are engaged to the inner shaft 22. The second ends of the proximal set of biasing members 42 engage the proximal balloon cone 32a in the expanded state and the second ends of the distal set of biasing members 42 engage the distal balloon cone 32b.

In this embodiment, there are three biasing members 42 but it is within the scope of the invention for there to be two, three, four, five, six, seven, eight or more biasing members 42. Examples of materials that can be used to make the biasing members 42 include, but are not limited to polymers, metals, alloys and any combination thereof. Examples of suitable polymers include, but are not limited to, polyamides, polyethylene (PE), Marlex high density polyethylene, polyetheretherketone (PEEK), polyamide (PI), and polyetherimide (PEI), liquid crystal polymers (LCP), acetal, polyoxymethylene (POM), polybutylene terephthalate (PBT), polyether block ester, polyether block amide (PEBA), fluorinated ethylene propylene (FEP), polypropylene (PP), polyvinylchloride (PVC), polyurethane, polytetrafluoroethylene (PTFE), polyimide, polyamide, polyphenylene sulfide (PPS), polyphenylene oxide (PPO), polysufone, nylon, perfluoro (propyl vinyl ether) (PFA), polyether-ester, polymer/metal composites, etc., or mixtures, blends or combinations thereof. One example of a suitable polyether block ester is available under the trade name ARNITEL, and one suitable example of a polyether block amide (PEBA) is available under the trade name PEBAX®, from ATOMCHEM POLYMERS, Birdsboro, Pa. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol. In at least one embodiment, the biasing members 42 are made of wire. In at least one embodiment, the biasing members 42 are made from shape memory material such as superelastic Nitinol or spring steel, or may be made of materials which are plastically deformable.

In FIG. 5, both the balloon 30 and the biasing members 42 are in an unexpanded state. When the balloon 30 is in an expanded state, the biasing members 42 are also in an expanded state. In at least one embodiment, the temperature of the inflation media used to inflate the balloon 30 causes shape member biasing members 42 to be in an expanded state. In the expanded state, the first and second ends of the biasing members 42 extend away from the inner shaft 22 and engage the sides of the balloon 30.

In this embodiment, when the biasing members 42 are in the expanded state, the first ends of the biasing members 42 engage the proximal cone 32a and the second ends of the biasing members 42 engage the distal cone 32b. In at least one embodiment, at least one end of the plurality of biasing members 42 is engaged to the proximal cone 32a and at least one end of the plurality of biasing members 42 is engaged to the distal cone 32b. Thus, some of the first ends of the biasing members 42 do not engage the proximal cone 32a and some of the second ends of the biasing members 42 do not engage the distal cone 32b.

Figure 6:
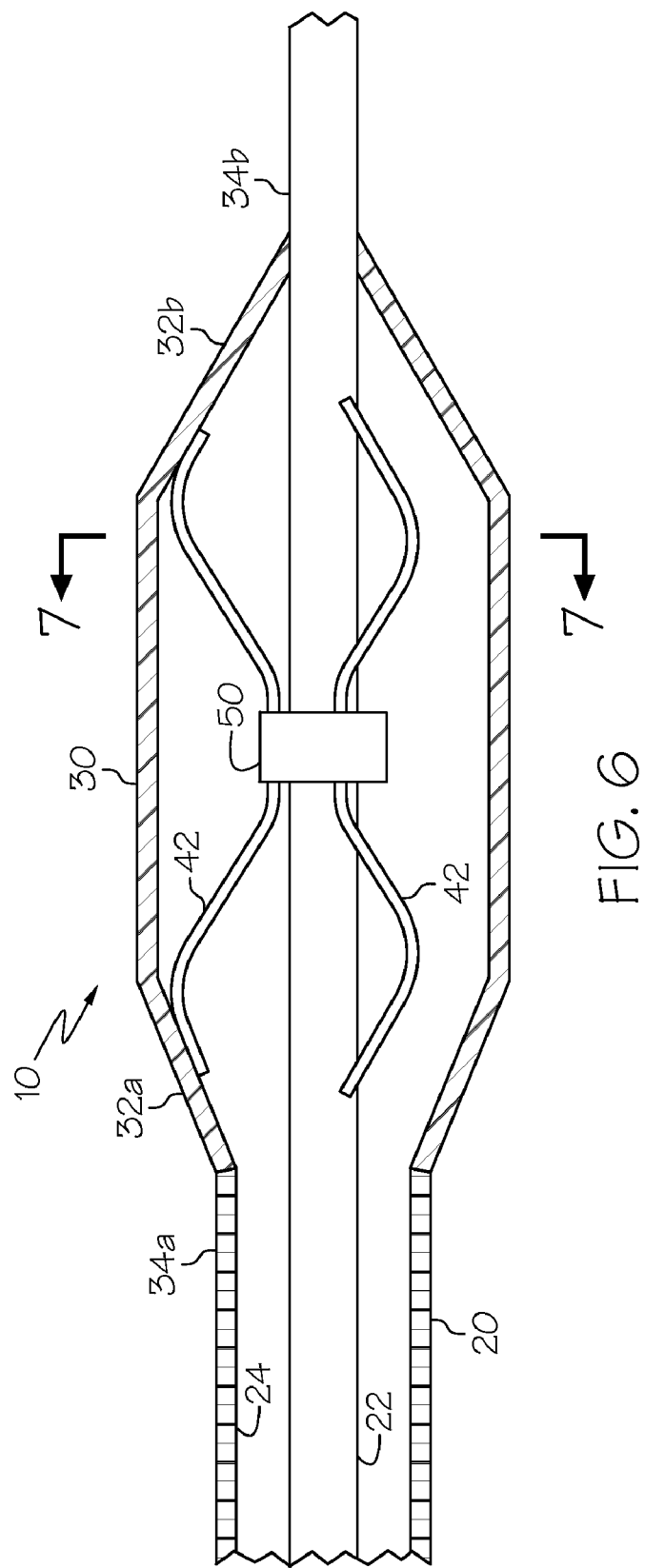
FIG. 6 is the longitudinal cross-section of the balloon catheter in FIG. 5 with both the biasing members and the balloon in an expanded state.
Figure 7:
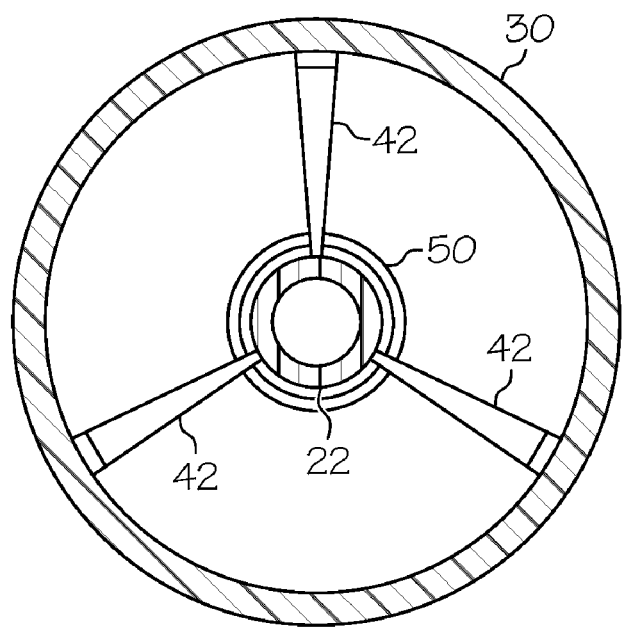
FIG. 7 is an end view of the balloon catheter in FIG. 5 taken at line 7-7 with a fully inflated balloon.

Thus, when the biasing members 42 are in an expanded state, the ends (first and/or second) of the biasing members 42 come into contact with the interior surface of the balloon 30. In at least one embodiment, the inner surface of the cones 32 is coated with an adhesive which fixedly engages the ends of the biasing members 42 to the inner surface of the cones 32 when the biasing members 42 contact the inner surface of the cones 32, as illustrated in FIG. 6. FIG. 7 is an end view of the balloon 30 in FIG. 6 taken at line 7-7 and illustrates the biasing members 42, in the expanded state, extending away from the inner shaft 22

In at least one embodiment, at least one portion of the inner surface of the balloon 30 has a layer of adhesive. Examples of adhesives that may be used are described in greater detail above. In at least one embodiment, the portions of the exterior surface of the biasing member 42 which contact the interior surface of the balloon 30 in the expanded state has an adhesive coating so that the biasing member 42 engages the interior surface of the balloon 30 in the expanded state.

Figure 8:
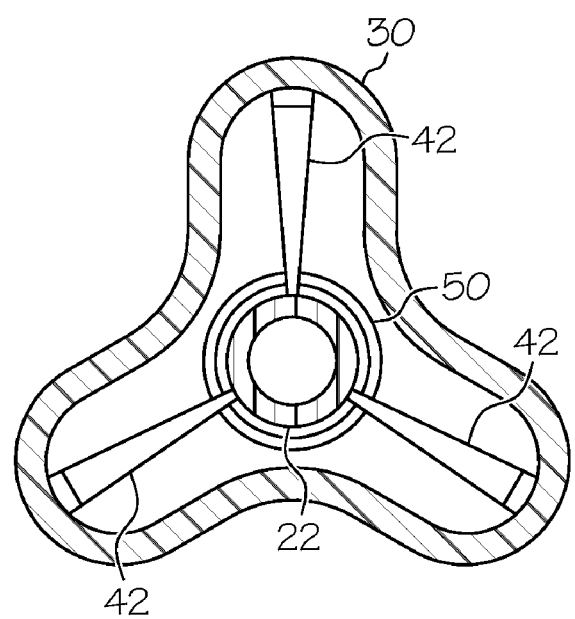
FIG. 8 is an end view of the balloon catheter in FIG. 6 taken at line 7-7 with the balloon in a partially expanded state.

In FIG. 8, the balloon 30 is in an intermediate expanded state. Note that the biasing members 42 continue to be in an expanded state. When the balloon 30 is in the intermediate expanded state and the biasing members 42 are in the expanded state, the biasing members 42 support the areas of the balloon 30 to which they are engaged and the other areas of the balloon 30 not supported by the biasing members 42 are drawn towards the inner shaft 42. In at least one embodiment, the balloon 30 is Y shaped when the balloon 30 is in an intermediate expanded state and the biasing members 42 are in an expanded state.

Figure 9:
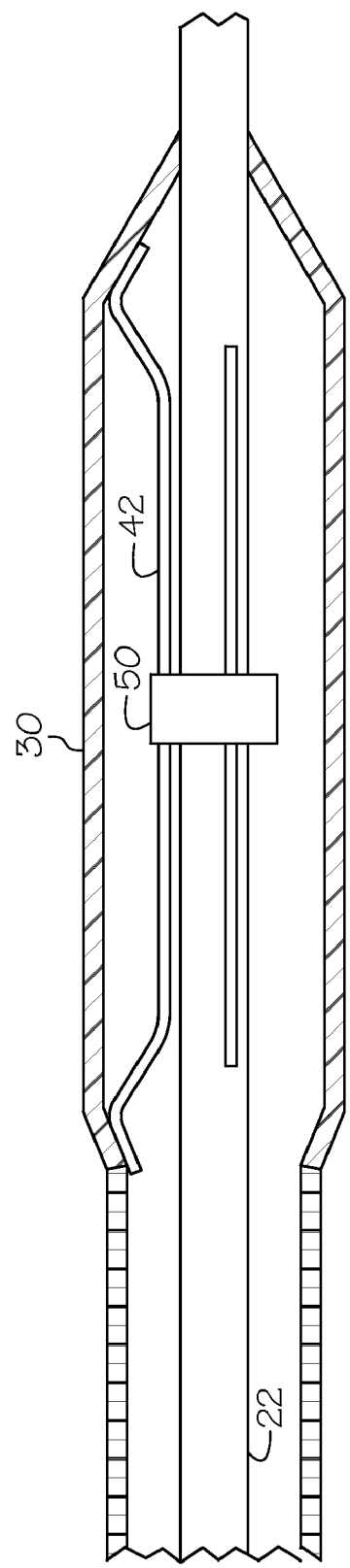
FIG. 9 is a longitudinal cross-section of a balloon catheter with both the biasing members and the balloon in an unexpanded state.

FIG. 9 is a longitudinal cross-section of the balloon catheter 10, showing the balloon 30 in a deflated state and the biasing members 42 in a second unexpanded state. When the balloon 30 is fully deflated, the springs 42 assume a second unexpanded state. In the second unexpanded state the biasing members 42 lay close to the inner shaft 22 but the ends of the biasing members 42 continue to be engaged to the interior surface of the balloon 30. Thus, when the biasing members 42 go from the expanded state to the second unexpanded state, the biasing members 42 pull the interior surfaces of the balloon 30 to which they are engaged towards the inner shaft 22.

In at least one embodiment, the biasing members 42 only have one unexpanded state. In this embodiment, the unexpanded state of the springs 42 is illustrated in FIG. 9. Thus, the ends of the biasing members 42 are engaged to the interior surface of the balloon 30 while in an unexpanded state, before the balloon 30 is in an expanded state, unlike the embodiment illustrated in FIG. 5 and described above. The inflation/deflation cycle in this embodiment begins with the balloon 30 and the biasing members 42 in an unexpanded state, as illustrated in FIG. 9. Then the balloon 30 is inflated so that the balloon 30 and biasing members 42 are in an expanded state, as illustrated in FIG. 6. Next, the balloon 30 is in an intermediate inflation state and the biasing members 42 are in an expanded state, as illustrated in the end view of FIG. 8. Finally, both the balloon 30 and the biasing members 42 return to the unexpanded state of FIG. 9.

Figure 10:
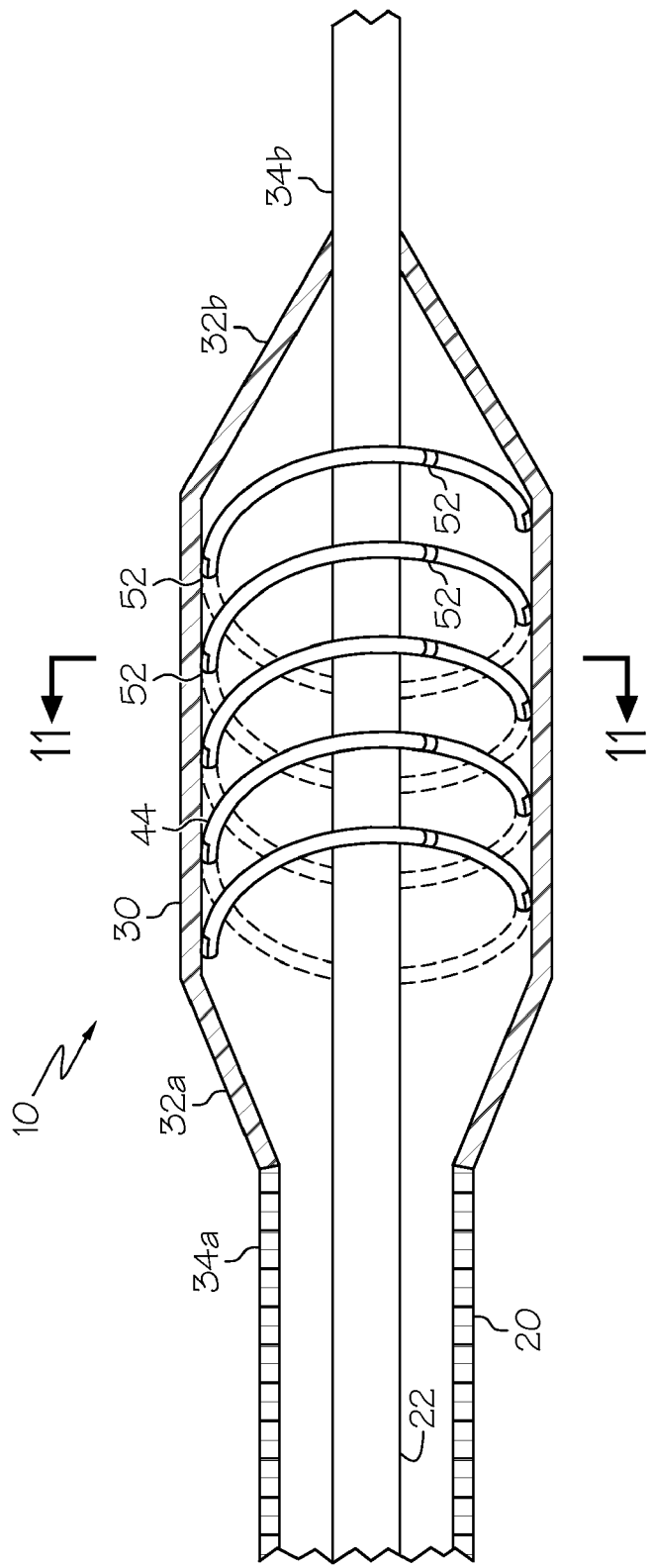
FIG. 10 is a partial longitudinal cross-section of a balloon catheter with a member engaged to the balloon.

FIG. 10 is a partial longitudinal cross-section of a balloon catheter 10 embodiment with a member 44 engaged to the balloon 30 at a plurality of engagement regions 52. The member 44 can have any shape so long as it aids in balloon re-wrap as discussed below. In at least one embodiment, the member 44 has a substantially round cross-section. In at least one embodiment, the member 44 has a ribbon shape. The balloon catheter 10 has an outer shaft 20, an inner shaft 22, a member 44 and a balloon 30. The outer shaft 20 defines an inflation lumen 24. The balloon 30 has a proximal waist 34a, proximal cone 32a, a distal cone 32b and a distal waist 34b. The middle section is between the proximal cone 32a and the distal cone 32b of the balloon 30. The balloon 30 has an expanded state and an unexpanded state.

The member 44 has an expanded state and a folded state. In both the expanded state and the folded state, the member 44 extends about the circumference of the balloon 30 and extends along a portion of the length of the balloon 30. In this embodiment, the member 44 forms a coil in the expanded state that extends from the proximal cone 32a to the distal cone 32b of the balloon 30, as illustrated in FIG. 10.

Figure 11:
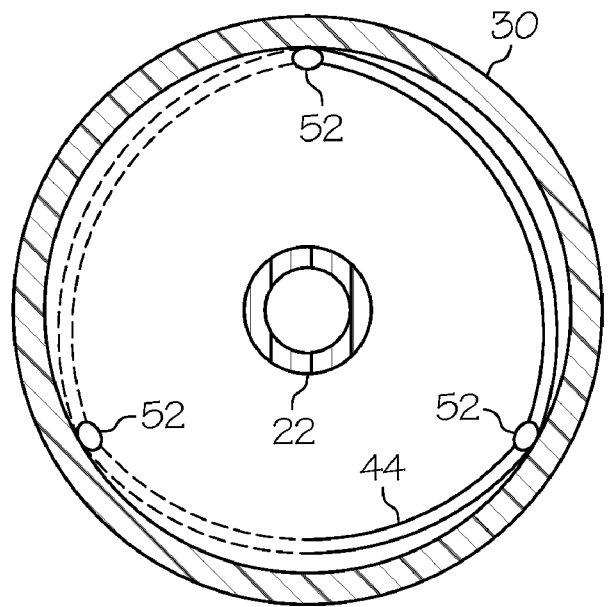
FIG. 11 is a cross-section of the balloon catheter in FIG. 10 taken at line 11-11.

The member 44 is engaged to the balloon 30 at a plurality of engagement regions 52. An engagement region 52 is an area of the balloon catheter 10 where the member 44 is engaged to the balloon 30. In this embodiment, the engagement regions 52 form three sets of engagement regions with each set of engagement regions on a longitudinal axis which is parallel to the inner shaft 22, as illustrated in FIG. 10. FIG. 11 is a cross-section of the balloon 30 in FIG. 10 taken at line 11-11.

In at least one embodiment, the member 44 is engaged to the balloon 30 at the engagement regions 52 by an adhesive. Examples of adhesives that may be used are described in greater detail above. In at least one embodiment, the member 44 is engaged to the balloon 30 at the engagement regions 52 by a curable/thermoset adhesive. In at least one embodiment, thermoplastic pressure sensitive adhesives are used to engage the member 44 to the balloon 30 at the engagement regions 52. In at least one embodiment, the member 44 is engaged to the balloon 30 at the engagement regions 52 by a pressure sensitive adhesive. In at least one embodiment, the member 44 has a plurality of regions with a layer of adhesive. In at least one embodiment, at least one portion of the inner surface of the balloon 30 has a layer of adhesive.

In at least one embodiment, the member 44 has an exterior surface, positioned next to, and engaged to, the interior surface of the balloon 30. Thus, in this embodiment, the member 44 has no discrete engagement regions 52 since the entire length of the member 44 is engaged to the interior surface of the balloon 30. In one embodiment, the exterior surface of the member 44 has an adhesive layer by which the member 44 engages the interior surface of the balloon 30. In one embodiment, the interior surface of the balloon 30 has an adhesive layer which engages the exterior surface of the member 44.

In at least one embodiment, the member 44 is made of a shape memory material such as superelastic Nitinol or spring steel, or may be made of materials which are plastically deformable. In this embodiment, the member 44 is in the expanded state when the balloon 30 is in an expanded state and in the folded state when the balloon 30 is in an unexpanded state. In at least one embodiment, the temperature of the inflation media determines whether the member 44 is in an expanded state or a folded state. In at least one embodiment, the member 44 is in a folded state at body temperature. In this embodiment, inflation media having a temperature less than the body temperature is used to inflate the balloon 30 and to cause the member 44 made of shape memory material transition from a folded state to an expanded state. In FIGS. 10 and 11 both the balloon 30 and the member 44 are in expanded states.

Figure 12:
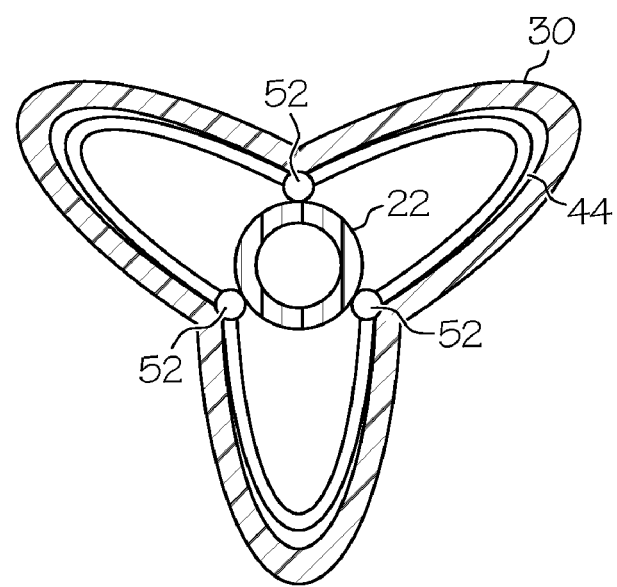
FIG. 12 is a cross-section of the balloon catheter in FIG. 10 taken at line 11-11 with the member in a folded configuration.

When the cool inflation media is withdrawn/evacuated from the balloon 30 the member 44 warms up to body temperature which causes the member 44 to be in the folded state, as illustrated in FIG. 12. The member 44 pulls the engagement regions 52 of the balloon 30 inwards towards the inner shaft 22 when the member 44 goes from an expanded state to a folded state. In at least one embodiment, the balloon 30 has a Y shape when the member 44 is in a folded state. The balloon 30 can have any shape when the member 44 is in the folded state so long as the balloon 30 can be rewrapped.

Figure 13:
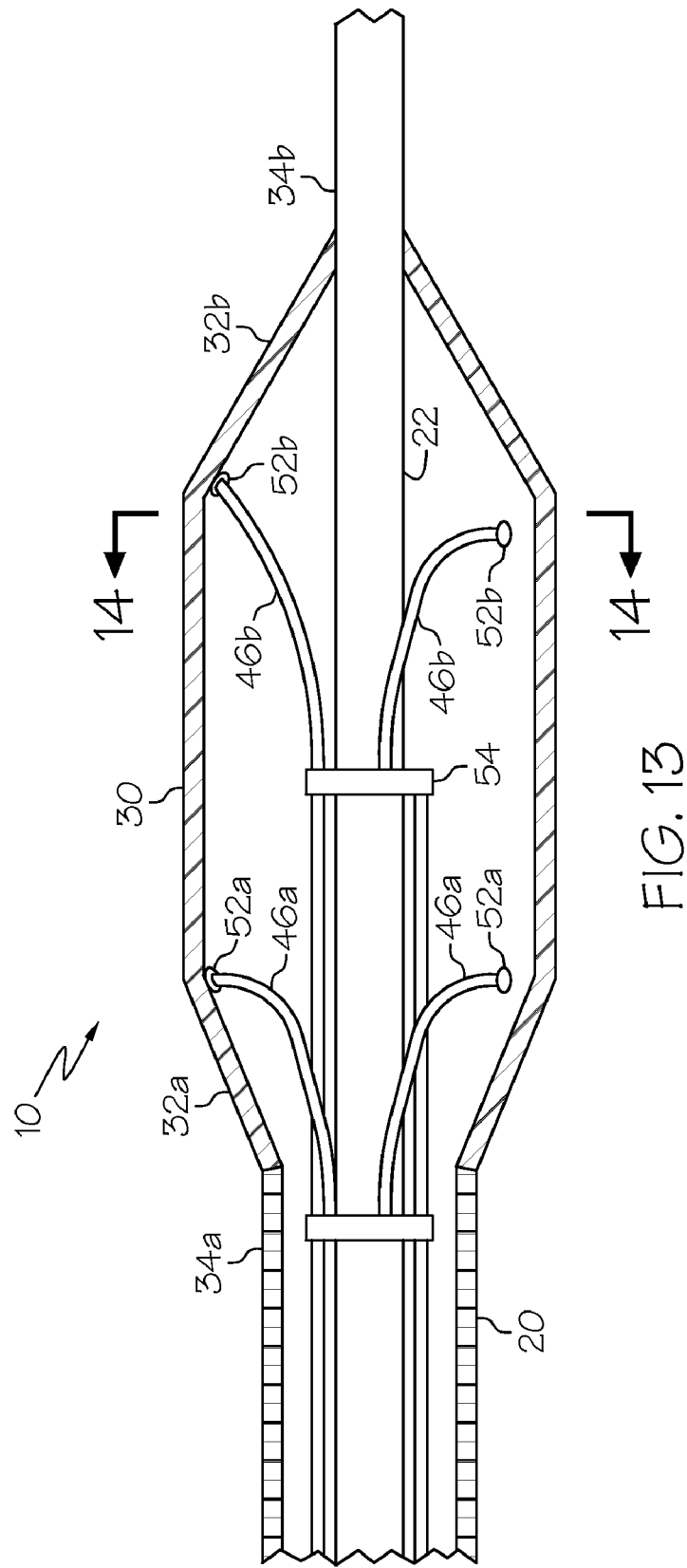
FIG. 13 is a longitudinal cross-section of a balloon catheter with two sets of tethers engaged to the cones of the balloon with the balloon in an expanded state.

FIG. 13 is a longitudinal cross-section of a balloon catheter 10 embodiment with two sets of tethers 46. The tethers 46 can have any shape so long as it aids in balloon re-wrap as discussed below. In at least one embodiment, the tethers 46 have a substantially round cross-section. In at least one embodiment, the tethers 46 have a ribbon shape. The balloon catheter 10 has an outer shaft 20, an inner shaft 22, a plunger 54 with a proximal set of tethers 46a and a distal set of tethers 46b and a balloon 30. The plunger 54 can have any shape so long as it can move proximally and distally along the inner shaft 22 and aid balloon re-wrap, as discussed below. The outer shaft 20 defines an inflation lumen 24. The balloon 30 has a proximal waist 34a, proximal cone 32a, a distal cone 32b and a distal waist 34b. The middle section is between the proximal cone 32a and the distal cone 32b of the balloon 30.

Figure 14:
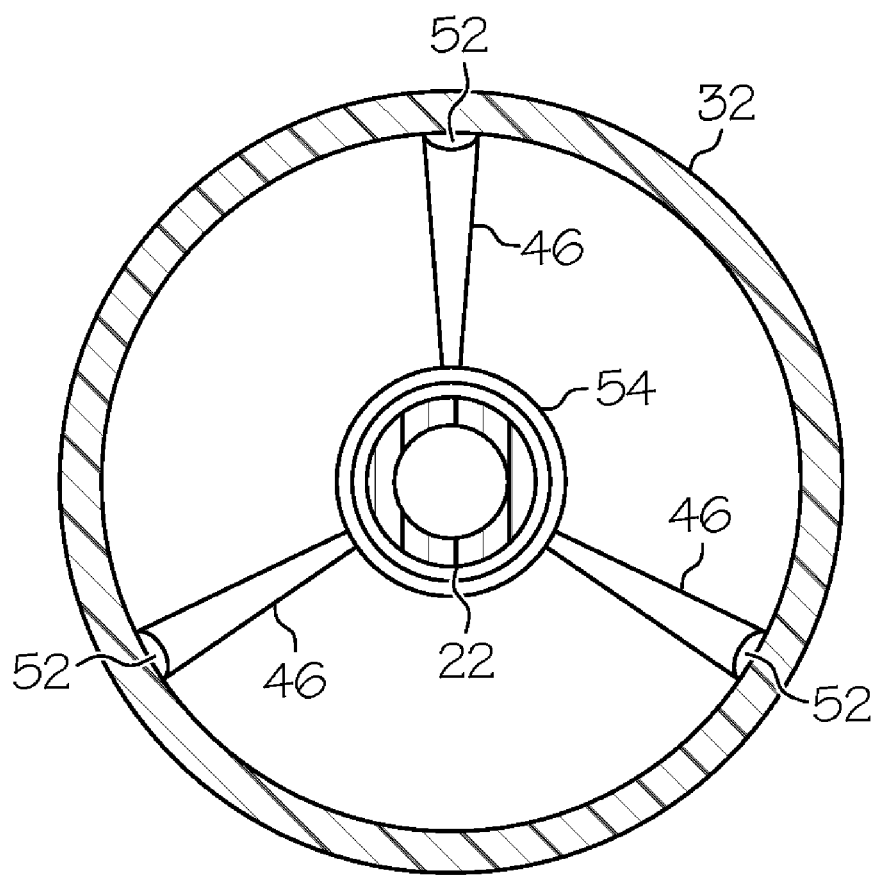
FIG. 14 is a cross-section of the balloon catheter in FIG. 13 taken at line 14-14.

In this embodiment, both the first and second sets of tethers 46a,b comprise three tethers 46. It is within the scope of the invention for a set of tethers 46 to have one, two, three, four, five, six, seven, eight or more tethers 46. Each tether 46 has a first end engaged to the plunger 54. The second ends of the proximal set of tethers 46a are engaged to the inside surface of the proximal balloon cone 32a at engagement regions 52a and the second ends of the distal set of tethers 46b are engaged to the inside surface of the distal balloon cone 32b at engagement regions 52b. An engagement region 52 is an area where a tether engages the balloon 30. In at least one embodiment, the second end region of the tether 46 is engaged to the balloon 30. The second end region includes the second end as well as a portion of the tether 46 before the second end. FIG. 14 is an end view of the balloon catheter in FIG. 13 taken at line 14-14 and shows the engagement regions 52 where the tethers 46 and the balloon cone 32 are engaged to one another.

Examples of adhesives that can be used to engage the tethers 46 to the balloon 30 are described in greater detail above. In at least one embodiment, the tethers 46 are engaged to the balloon 30 by a pressure sensitive adhesive. In at least one embodiment, thermoplastic pressure sensitive adhesives are used to engage the tethers 46 to the balloon 30. In at least one embodiment, the tethers 46 are engaged to the balloon 30 by a curable/thermoset adhesive. In at least one embodiment, the balloon catheter 10 has one set of tethers 46 engaged to the proximal balloon cone 32a. In at least one embodiment, the balloon catheter 10 has one set of tethers 46 engaged to the distal balloon cone 32b.

In FIG. 14, the plunger 54 is positioned about the inner shaft 22 but not engaged to the inner shaft 22 so that the plunger 54 can move both proximally and distally along the inner shaft 22. In at least one embodiment, application of a vacuum, such as occurs during deflation, causes the plunger 54 to slide in a proximal direction, thereby pulling the tethers 46 in a proximal direction. The movement of the plunger 54 in the proximal direction necessarily pulls the tethers 46 in the proximal direction and causes the second ends of the tethers 46 to move closer to the inner shaft 22. Since the second ends of the tethers 46 are engaged to the interior surface of the balloon 30 at engagement regions 52, as the second ends of the tethers 46 move closer to the inner shaft 22, the engagement regions 52 move closer to the inner shaft 22. This movement of the balloon 30 towards the inner shaft 22 causes the balloon 30 to collapse and helps with refolding the balloon 30.

Materials that can be used to make the tethers 46 include, but are not limited to polymers, mylar fibers or nylon fiber/thread. In at least one embodiment, the tethers 46 are made of wire. In at least one embodiment, the tethers 46 are made of a polymer. Examples of suitable polymers include, but are not limited to, polyamides, polyethylene (PE), Marlex high density polyethylene, polyether-etherketone (PEEK), polyamide (PI), and polyetherimide (PEI), liquid crystal polymers (LCP), acetal, polyoxymethylene (POM), polybutylene terephthalate (PBT), polyether block ester, polyether block amide (PEBA), fluorinated ethylene propylene (FEP), polypropylene (PP), polyvinylchloride (PVC), polyurethane, polytetrafluoroethylene (PTFE), polyimide, polyamide, polyphenylene sulfide (PPS), polyphenylene oxide (PPO), polysufone, nylon, perfluoro (propyl vinyl ether) (PFA), polyether-ester, polymer/metal composites, etc., or mixtures, blends or combinations thereof. One example of a suitable polyether block ester is available under the trade name ARNITEL, and one suitable example of a polyether block amide (PEBA) is available under the trade name PEBAX®, from ATOMCHEM POLYMERS, Birdsboro, Pa. In at least one embodiment, the second end of the tethers 46 are made of a different material than the rest of the tether 46.

Materials that can be used to make the plunger 54 include, but are not limited to, polymers, metals, and alloys. Examples of suitable polymers include, but are not limited to, polyamides, polyethylene (PE), Marlex high density polyethylene, polyether-etherketone (PEEK), polyamide (PI), and polyetherimide (PEI), liquid crystal polymers (LCP), acetal, polyoxymethylene (POM), polybutylene terephthalate (PBT), polyether block ester, polyether block amide (PEBA), fluorinated ethylene propylene (FEP), polypropylene (PP), polyvinylchloride (PVC), polyurethane, polytetrafluoroethylene (PTFE), polyimide, polyamide, polyphenylene sulfide (PPS), polyphenylene oxide (PPO), polysufone, nylon, perfluoro (propyl vinyl ether) (PFA), polyether-ester, polymer/metal composites, etc., or mixtures, blends or combinations thereof. One example of a suitable polyether block ester is available under the trade name ARNITEL, and one suitable example of a polyether block amide (PEBA) is available under the trade name PEBAX®, from ATOMCHEM POLYMERS, Birdsboro, Pa. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

In at least one embodiment, the interior surface of the plunger 54 has a lubricant. Suitable lubricants include, but are not limited to, fluoropolymer, a silicone coating such as MICROGLIDE™, or HYDROCOAT™ silicones, polyvinyl pyrrolidone, PPO (polypropylene oxide), Teflon® available from DuPont De Nemours, Wilmington, Del. U.S., hydrophobic materials such as silicone lubricant dispersion PN 4097, available from Applied Silicone Corp., Ventura, Calif. U.S., or a hydrophilic materials such as hydrogel available from Hydromer, Branchburg, N.J. U.S., hydrophilic polyacrylamide, or lubricious coatings such as those available from Hydro-Silk of Merritt Island, Fla., under the trade name TUA Systems. Additionally, BioSlide™ coating produced by SciMed made be used as well. BioSlide™ is a hydrophilic, lubricious coating comprising polyethylene oxide and neopentyl glycol diacrylate polymerized in a solution of water and isopropyl alcohol in the presence of a photoinitiator such as azobisisobutronitrile. Other hydrogels such as PEG (polyethylene glycol), PEO/PPO/PEO-polyethylene oxide/polypropylene oxide/polyethylene oxide triblock polymer manufactured by BASF or PPO/PEO/PPO may also be used.

Figure 15:
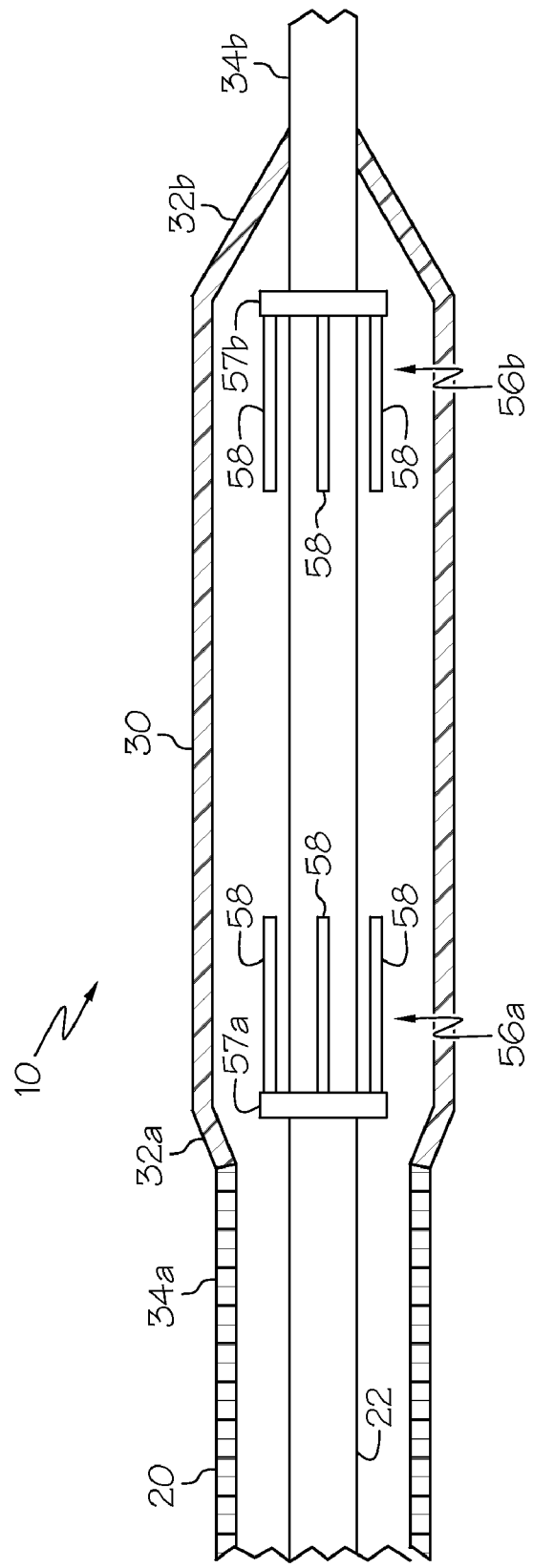
FIG. 15 is a longitudinal cross-section of a balloon catheter with two sets of inner skeletons in a folded state.

FIG. 15 is a longitudinal cross-section of a balloon catheter 10 embodiment with two inner balloon skeletons 56 positioned about the inner shaft 22, between the inner shaft and the balloon 30. The balloon catheter 10 has an outer shaft 20, an inner shaft 22, a proximal inner balloon skeleton 56a, a distal inner balloon skeleton 56b and a balloon 30. The outer shaft 20 defines an inflation lumen 24. The balloon 30 has a proximal waist 34a, proximal cone 32a, a middle section, a distal cone 32b and a distal waist 34b. The middle section is between the proximal cone 32a and the distal cone 32b of the balloon 30. The balloon 30 is positioned about the balloon region of the inner shaft 22 and has an expanded state and an unexpanded state. The balloon region of the inner shaft 22 extends from the proximal end of the proximal waist 34a of the balloon 30 to the distal end of the distal waist 34b of the balloon 30.

The body 57 of each skeleton 56 is engaged to the balloon region of the inner shaft 22 and each skeleton 56 comprises at least one prong 58. The body 57 functions to hold the prongs 58 at a specific location on the balloon region of the inner shaft 22. Thus, the body 57 can have any shape and width. In this embodiment, the body 57 of the skeleton 56 is a circumferential rectangular band. In at least one embodiment, the body 57 of the skeleton 56 is a non-circumferential band. The body 57 of the skeleton 56 may be made from polymers, metals, alloys and any combination thereof. Examples of suitable polymers include, but are not limited to, polyamides, polyethylene (PE), Marlex high density polyethylene, polyether-etherketone (PEEK), polyamide (PI), and polyetherimide (PEI), liquid crystal polymers (LCP), acetal, polyoxymethylene (POM), polybutylene terephthalate (PBT), polyether block ester, polyether block amide (PEBA), fluorinated ethylene propylene (FEP), polypropylene (PP), polyvinylchloride (PVC), polyurethane, polytetrafluoroethylene (PTFE), polyimide, polyamide, polyphenylene sulfide (PPS), polyphenylene oxide (PPO), polysufone, nylon, perfluoro (propyl vinyl ether) (PFA), polyether-ester, polymer/metal composites, etc., or mixtures, blends or combinations thereof. One example of a suitable polyether block ester is available under the trade name ARNITEL, and one suitable example of a polyether block amide (PEBA) is available under the trade name PEBAX®, from ATOMCHEM POLYMERS, Birdsboro, Pa. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

Although the embodiment in FIG. 15 has four prongs 58, it is within the scope of the invention for a skeleton 56 to have one, two, three, four, five, six, seven, eight or more prongs 58. A prong 58, as used in this application, is any member, projection, coil, spine, spike, tine, or other means, manufactured and designed so that the second end or the second end region of the prong 58 engages the interior of the balloon 30. In this embodiment, each prong 58 has a first end engaged to the body 57 of the skeleton 56. Note that the prongs 58 can be engaged to the body 57 by any suitable means. In at least one embodiment, the first ends of the prongs 58 are engaged to the balloon region of the inner shaft 22, therefore the skeleton 56 does not have a body 57.

In at least one embodiment, the balloon catheter 10 has two skeletons 56 and each skeleton 56 has the same number of prongs 58, as illustrated in FIG. 15. In at least one embodiment, the balloon catheter 10 has two skeletons 56 and each skeleton 56 has a different number of prongs 58. In this embodiment, each skeleton 56 has four prongs 58 positioned at equal intervals about the circumference of the inner shaft 22. In at least one embodiment, the balloon catheter 10 has one skeleton 56. In one embodiment, the skeleton 56 is positioned at the proximal end of the balloon region of the inner shaft 22. In one embodiment, the skeleton 56 is positioned at the distal end of the balloon region of the inner shaft 22.

Figure 16:
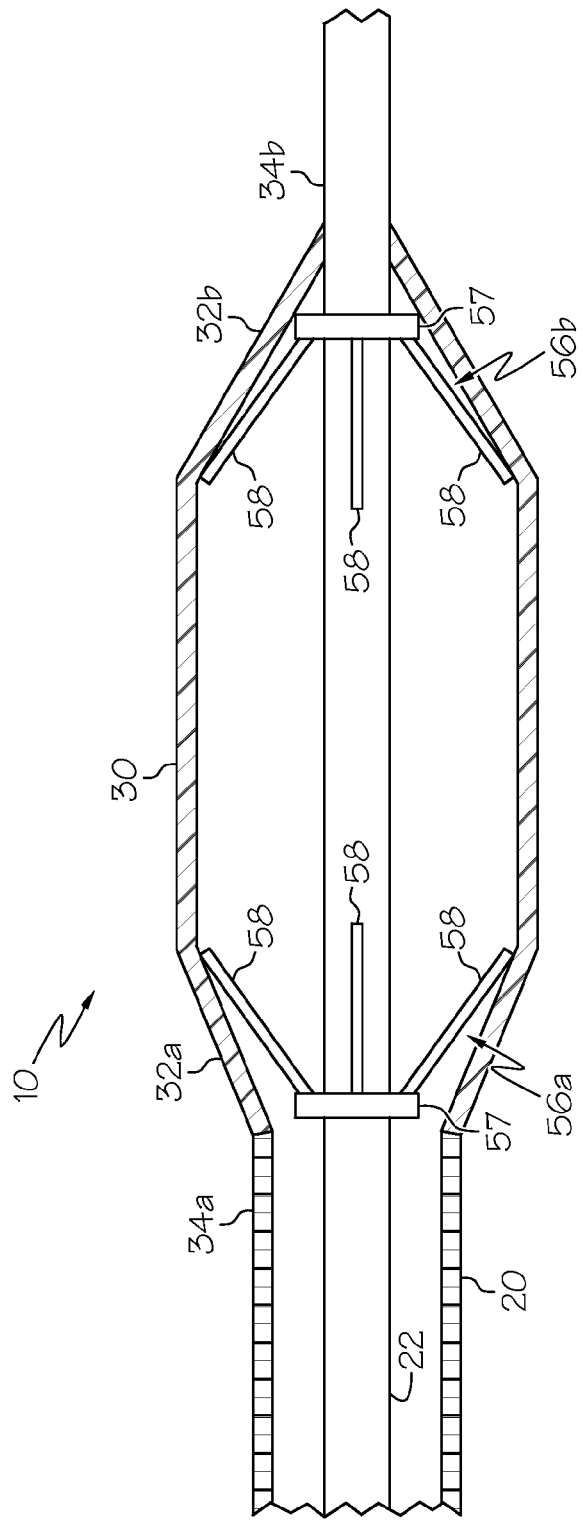
FIG. 16 is a longitudinal cross-section of the balloon catheter in FIG. 15 with the two sets of inner skeletons in an expanded state.

Each prong 58 has an unexpanded state and an expanded state. In FIG. 15 both the balloon 30 and the prongs 58 are in an unexpanded state, while in FIG. 16 both the balloon 30 and the prongs 58 are in an expanded state. When the prongs 58 are in an expanded state, at least a portion of the second end or the second end region of each prong 58 is engaged to the inner surface of the balloon 30. In at least one embodiment, at least a portion of the second end of each prong 58 is engaged to the inner surface of a balloon cone 32. In at least one embodiment, at least a portion of the second end of each prong 58 is engaged to the inner surface of the middle section of the balloon 30.

In at least one embodiment, the second end or the second end region of each prong 58 has an adhesive so that the second end region of the prong 58 engages the inner surface of the balloon 30. Examples of adhesives that may be used on the second end/second end region of each prong 58 are described in greater detail above. In at least one embodiment, the second end or second end region of the prong 58 is engaged to the balloon 30 by a pressure sensitive adhesive. In at least one embodiment, thermoplastic pressure sensitive adhesives are used to engage the prongs 58 to the balloon 30. In at least one embodiment, the prongs 58 are engaged to the balloon by a curable/thermoset adhesive.

Figure 17:
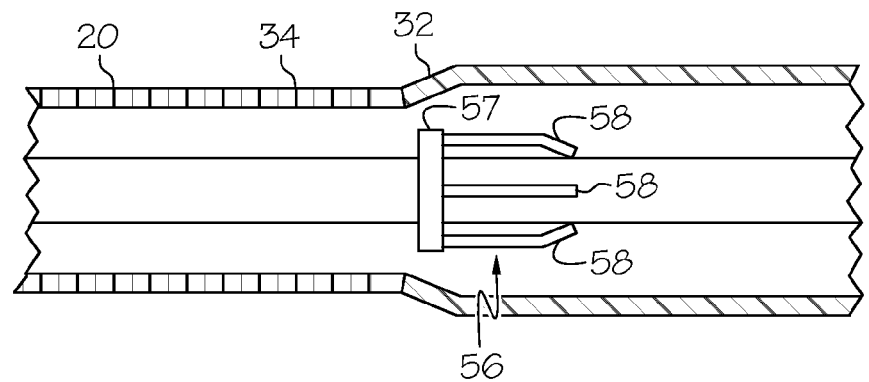
FIG. 17 is a longitudinal cross-section of a portion of a balloon catheter with a second embodiment of the inner skeleton in an unexpanded state.
Figure 18:
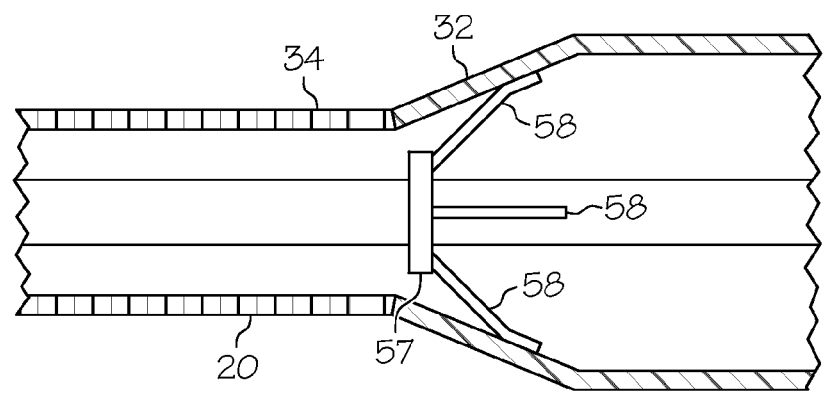
FIG. 18 is the longitudinal cross-section of FIG. 18 with the second embodiment of the inner skeleton in an expanded state.

The prongs 58 can have any shape so long as at least a portion of the second end region of each prong 58, in the expanded state engages the inner surface of a portion of the balloon 30. The prongs 58 in FIGS. 17 and 18 have a second end region, which extends from the bend to the second end of the prong 58. A prong 58 with a bend along the length of the prong 58 provides a greater surface area with which the prong 58 can engage the inner surface of the balloon 30 when the each prong 58 is in an expanded state. The angle of the bend in the prong 58 is an obtuse angle less than 90 degrees. In at least one embodiment, the angle of the bend in the prong 58 matches the angle of the cone 32. The length between the second end and the bend in the prong 58 can be varied so that the greater the length the greater the engagement area between the prong 58 and the inner surface of the cone 32. However, the angle of the bend and the length between the second end and the bend will affect how close the prong 58 will be to the inner shaft 22, as is illustrated in FIG. 17. Due to the bend in the prong 58, the second end region of the prong 58 angles towards the inner shaft 22 when the prong 58 is in an unexpanded state.

The prongs 58 may be made from polymers, metals, alloys and any combination thereof. Examples of suitable polymers include, but are not limited to, polyamides, polyethylene (PE), Marlex high density polyethylene, polyether-etherketone (PEEK), polyamide (PI), and polyetherimide (PEI), liquid crystal polymers (LCP), acetal, polyoxymethylene (POM), polybutylene terephthalate (PBT), polyether block ester, polyether block amide (PEBA), fluorinated ethylene propylene (FEP), polypropylene (PP), polyvinylchloride (PVC), polyurethane, polytetrafluoroethylene (PTFE), polyimide, polyamide, polyphenylene sulfide (PPS), polyphenylene oxide (PPO), polysufone, nylon, perfluoro (propyl vinyl ether) (PFA), polyether-ester, polymer/metal composites, etc., or mixtures, blends or combinations thereof. One example of a suitable polyether block ester is available under the trade name ARNITEL, and one suitable example of a polyether block amide (PEBA) is available under the trade name PEBAX®, from ATOMCHEM POLYMERS, Birdsboro, Pa. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol. In at least one embodiment, the prong 58 is made from a different material than the body 57.

In at least one embodiment, the prong 58 embodiments described above are made of shape memory material such as superelastic Nitinol or spring steel, or may be made of materials which are plastically deformable. At body temperature, the prongs 58 are in either a first or second unexpanded state while at temperatures below body temperature, the prongs 58 are in an expanded state. Therefore, the prongs 58 are in a first unexpanded state when the balloon catheter 10 is advanced to the desired location within the body. Then, inflation media at a temperature below body temperature is used to inflate the balloon 30. The temperature of the inflation media causes the prongs 58 to transition from the first unexpanded state to an expanded state where the prongs 58 become engaged to the interior surface of the balloon 30. When the cool inflation media is withdrawn/evacuated during deflation of the balloon 30, the prongs 58 warm up to body temperature and transition to a second unexpanded state. When the prongs 58 transition to the second unexpanded state, the second ends of the prongs 58 pull the balloon 30 towards the inner shaft 22. Thus, in the first unexpanded state, the prongs 58 are not engaged to the interior surface of the balloon 30 but in the second unexpanded state, the prongs 58 are engaged to the interior surface of the balloon 30.

In at least one embodiment, not shown, each prong 58 is a coil having a second end and has an unexpanded state and an expanded state. The second end of the coil shaped prong 58 is engaged to the inner surface of the balloon 30 when the prong 58 is in both the unexpanded state and the expanded state. Expansion of the balloon 30 to the expanded state causes the coil shaped prong 58 to assume an expanded state. Because the coil shaped prong 58 prefers to be in an unexpanded state, when the pressure against the sides of the balloon 30 is reduced sufficiently during deflation, the coil shaped prong 58 will transition to an unexpanded state and pull the balloon 30 towards the inner shaft 22. Note that the force of the coil shaped prong 58 in the expanded state must be modulated so that a hole is not formed in the side of the balloon 30 due to the downward force/tension of the coil shaped prong 58.

Figure 19:
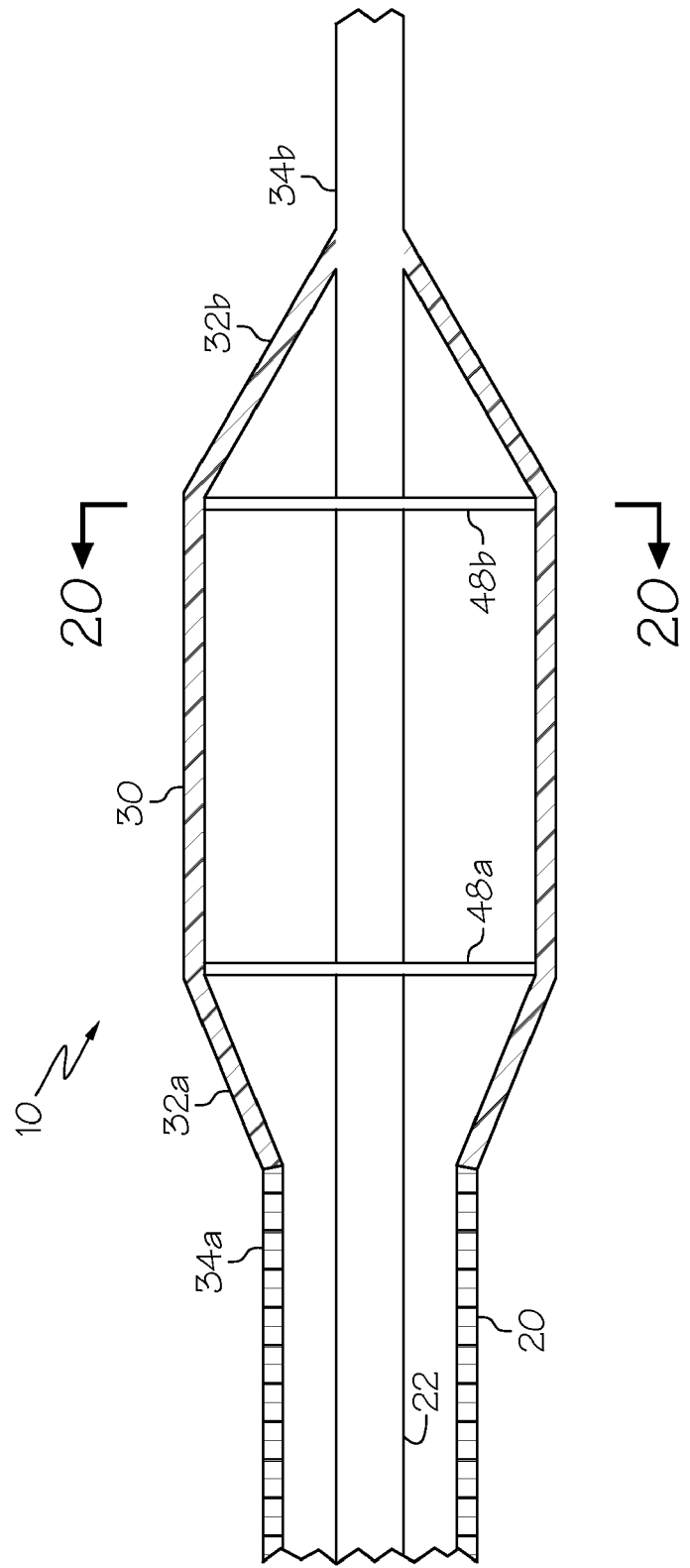
FIG. 19 is a partial longitudinal cross-section of a balloon catheter with two rings, with the rings in an expanded state.

FIG. 19 is a partial longitudinal cross-section of a balloon catheter 10 embodiment that has a balloon 30 with rings 48. The balloon catheter 10 has an outer shaft 20, an inner shaft 22, a proximal inner balloon skeleton 56a, a distal inner balloon skeleton 56b and a balloon 30. The outer shaft 20 defines an inflation lumen 24. The balloon 30 has a proximal waist 34a, proximal cone 32a, a middle section, a distal cone 32b, a distal waist 34b, a proximal ring 48a and a distal ring 48b. The middle section is between the proximal cone 32a and the distal cone 32b of the balloon 30. Note that the proximal ring 48a is positioned at the proximal end of the middle section and the distal ring 48b is positioned at the distal end of the middle section. Although the balloon catheter 10 in FIG. 19 has two rings 48, it is within the scope of the invention for there to be one, two, three, four, five, six, seven, eight or more rings 48.

Figure 20:
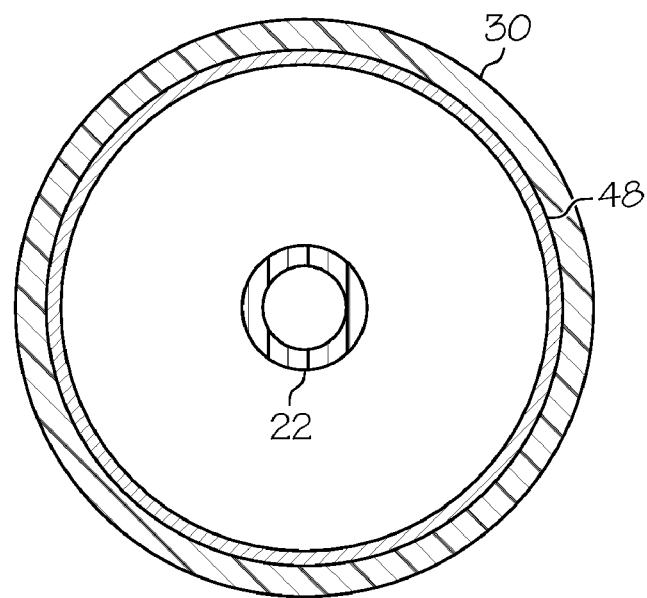
FIG. 20 is a cross-section of the balloon catheter in FIG. 19 taken at line 20-20 with the ring in an expanded state.

In FIGS. 19 and 20 the rings 48 and the balloon 30 are in an expanded state. The rings 48 can have any longitudinal length and thickness. In at least one embodiment, the rings 48 each have a longitudinal length ranging from 0.0025 inches or 0.06 mm to 0.197 inches or 5 mm. In at least one embodiment, each ring 48 has the same longitudinal length. In at least one embodiment, each ring 48 has a different longitudinal length. In at least one embodiment, each ring 48 has a thickness ranging from 0.0025 inches or 0.06 mm to 0.0394 inches or 1.0 mm. FIG. 20 is a cross-section of the balloon catheter 10 in FIG. 19 taken at line 20-20. In at least one embodiment, the rings 48 are engaged to the inner surface of the balloon 30. In at least one embodiment, the balloon 30 is manufactured so that the rings 48 form a part of the balloon wall.

Figure 21:
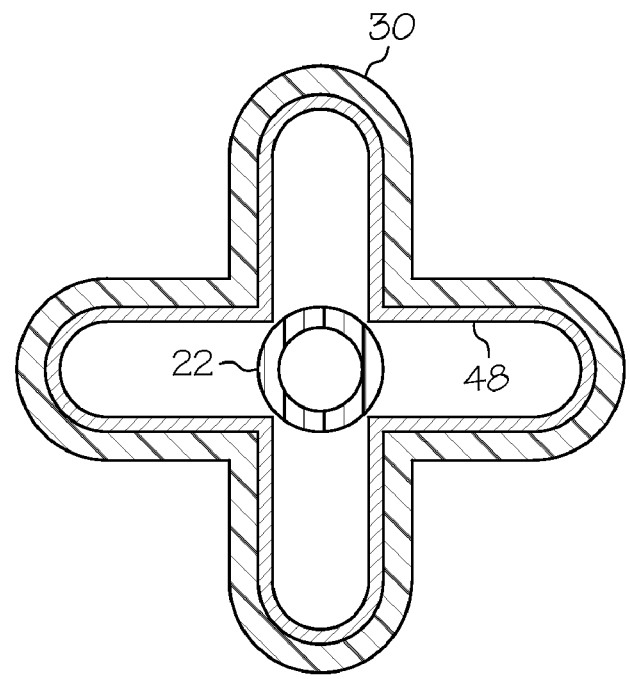
FIG. 21 is a cross-section of the balloon catheter in FIG. 19 taken at line 20-20 with the ring in a folded state.

In FIG. 21 the ring 48 is in a folded state. In at least one embodiment, the ring 48 has a star or wing shape in the folded state. The ring 48 is in the folded state when at body temperature and transitions to the expanded state due to inflation pressure.

In at least one embodiment, the rings 48 are manufactured from shape memory material. In this embodiment, the rings 48 are in a folded state at body temperature and in an expanded state at temperatures below body temperature. Thus, the rings 48 are in a folded state as the balloon catheter 10 is positioned within the body lumen. Inflation media at a temperature cooler than body temperature is used to inflate the balloon 30. The cool inflation media causes the rings 48 to transition to an expanded state. The rings 48 heat back to body temperature and then transition back to the folded state when the cool inflation media is removed/evacuated from the balloon 30. This facilitates the refolding of the balloon 30.

The rings 48 may be made from shape memory materials such as superelastic Nitinol or spring steel, or may be made of materials which are plastically deformable. In at least one embodiment, the rings 48 are manufactured from Niti wire.

In at least one embodiment, the balloon 30 is manufactured from compliant material for example, but not limited to, nylon, and polyamines. In at least one embodiment, the balloon 30 is made of semi-compliant material, for example, but not limited to, ethylene-vinyl acetate, polyvinyl chloride (PVC), olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins. In at least one embodiment, the balloon 30 is manufactured from non-compliant material, for example, but not limited to, polyethylene terephthalates, polyacrylenesulfide, and copolyesters. Other suitable balloon materials may also be used.

In some embodiments the delivery system or other portion of the assembly may include one or more areas, bands, coatings, members, etc. that is (are) detectable by imaging modalities such as X-Ray, MRI, ultrasound, etc. In some embodiments at least a portion of the assembly is at least partially radiopaque.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A balloon catheter, the balloon catheter comprising:
an inner shaft, a balloon and at least one biasing member, the inner shaft comprising a balloon region about which the balloon is positioned;
the balloon comprising an inner surface and having an unexpanded state, an expanded state, and an intermediate expanded state, the balloon having a first configuration in the expanded state and a second configuration in the intermediate expanded state, the first configuration being different than the second configuration, the second configuration being a non-round shaped configuration;

each biasing member positioned about the balloon region of the inner shaft between the inner shaft and the balloon, a portion of each biasing member engaged to the balloon region of the inner shaft, each biasing member made from a shape memory material, each biasing member having an unexpanded state and an expanded state, each biasing member being in the unexpanded state when the balloon is in the unexpanded state, each biasing member being in the expanded state when the balloon is in the expanded state and when the balloon is in the intermediate expanded state;

when the balloon is in the intermediate expanded state, portions of the balloon are supported by the at least one biasing member and portions of the balloon are unsupported by the at least one biasing member.

2. The balloon catheter of claim 1, the at least one biasing member comprising a first biasing member, a second biasing member, and a third biasing member.

3. The balloon catheter of claim 1, a portion of each biasing member being engaged to the inner surface of the balloon when the balloon is in the deflated state.

4. The balloon catheter of claim 2, the second configuration being Y-shaped.

5. The balloon catheter of claim 1, the balloon catheter further comprising a band, the band engaging the first biasing member to the inner shaft.

6. A balloon catheter, the balloon catheter comprising a shaft, a balloon, and a member, the balloon having a circumference, a length, and an inner surface, the balloon being disposed about the shaft; and the member having a length, a plurality of engagement regions along the length of the member, the member engaged to the inner surface of the balloon at each of the plurality of engagement regions, the member having an expanded state and a folded state, in both the expanded state and the folded state the member extends about the circumference of the balloon along at least a portion of the length of the balloon, when the member is in the folded state the plurality of engagement regions being disposed adjacent to the shaft and when the member is in the expanded state the plurality of engagement regions being disposed away from the shaft.

7. The balloon catheter of claim 6, the member being made of a shape memory material.

8. The balloon catheter of claim 6, the expanded configuration being a coil.

9. The balloon catheter of claim 8, the member in the folded state forming a Y-shaped balloon.

10. The balloon catheter of claim 6, the member made of shape memory material.

11. A balloon catheter, the balloon catheter comprising an inner shaft, a balloon, a plunger and a first set of tethers, the plunger slidably positioned about the inner shaft, the plunger having a distal end;

the balloon having an inner surface, an expanded state and a deflated state;

each tether having a first end and a second end, the first end engaged to a portion of the plunger, the second end engaged to the inner surface of the balloon at an engagement point;

the distal end of the plunger having a first position when the balloon is in the expanded state and a second position when the balloon is in the deflated state, the first position being distal to the second position; and the second ends of the tethers being closer to the inner shaft when the distal end of the plunger is in the second position than when the plunger is in the first position.

12. The balloon catheter of claim 11, further comprising a second set of tethers, each tether having a first end and a second end, the first ends being engaged to a portion of the plunger, the balloon having a proximal cone and a distal cone, the second ends of the first set of tethers being engaged to the inner surface of the proximal cone, and the second ends of the second set of tethers being engaged to the inner surface of the distal cone.

13. The balloon catheter of claim 11, the tethers made of wire.

14. A balloon catheter, the balloon catheter comprising an inner shaft, a balloon and a first skeleton, the inner shaft comprising a balloon region about which the balloon is positioned;

the balloon having an expanded state and a deflated state, the balloon being in the deflated state after the expanded state; and the first skeleton comprising at least one prong, at least a portion of the first skeleton being engaged to a portion of the balloon region of the inner shaft each prong having a first unexpanded state, a second unexpanded state, and an expanded state, each prong being in the expanded state when the balloon is in the expanded state, the at least one prong being in the first unexpanded state before the balloon is in the expanded state and in the second unexpanded state when the balloon is in the deflated state, each prong being positioned between the inner shaft and the balloon in the first unexpanded state, and a portion of each prong being engaged to a portion of the inner surface of the balloon only in the expanded and second unexpanded states.

15. The balloon catheter of claim 14, the balloon catheter further comprising a second skeleton comprising at least one prong, at least a portion of the second skeleton engaged to a portion of the balloon region of the inner shaft different than the portion of the balloon region of the inner shaft to which the first skeleton is engaged, each prong of the second skeleton having a first unexpanded state, a second unexpanded state, and an expanded state, each prong being in the expanded state when the balloon is in the expanded state, the at least one prong being in the unexpanded state when the balloon is in the deflated state each prong is positioned between the inner shaft and the balloon in the first unexpanded state, a portion of each prong being engaged to a portion of the inner surface of the balloon only in the expanded and second unexpanded states.

16. The balloon catheter of claim 14, the at least one prong pulling the balloon towards the inner shaft when the at least one prong goes from the expanded state to the second unexpanded state.

17. A balloon catheter, the balloon catheter comprising an inner shaft and a balloon disposed about the inner shaft;

the balloon having a proximal cone, a middle section, a distal cone and comprising a first ring and a second ring, the middle section positioned between the proximal cone and the distal cone, the middle section having a first end and a second end, the balloon having an expanded state; and the first ring positioned at the first end of the middle section and the second ring positioned at the second end of the middle section, each ring having a folded state and an expanded state, portions of each ring being closer to the inner shaft when the ring is in the folded state than when the ring is in the expanded state, each ring being in the expanded state when the balloon is in the expanded state.

18. The balloon catheter of claim 17, the first and second rings made of shape memory material.

19. The balloon catheter of claim 17, the balloon having a wall, the first and second rings forming a portion of the wall of the balloon.

20. The balloon catheter of claim 17, each ring having a round shape in the expanded state.

21. The balloon catheter of claim 18, wherein an increase in pressure causes each ring to be in an expanded state.

22. The balloon catheter of claim 18, wherein each ring is in a folded state at body temperature.

* * * * *